United States Patent
Sadoun

(10) Patent No.: US 8,507,578 B2
(45) Date of Patent: Aug. 13, 2013

(54) COMPOSITE CERAMIC BLOCK

(76) Inventor: Michael Sadoun, Paris (FR)

(*) Notice: Subject to any disclaimer, the term of this patent is extended or adjusted under 35 U.S.C. 154(b) by 46 days.

(21) Appl. No.: 13/063,365

(22) PCT Filed: Sep. 11, 2009

(86) PCT No.: PCT/IB2009/053993
§ 371 (c)(1), (2), (4) Date: Jun. 1, 2011

(87) PCT Pub. No.: WO2010/029515
PCT Pub. Date: Mar. 18, 2010

(65) Prior Publication Data
US 2011/0229858 A1 Sep. 22, 2011

(30) Foreign Application Priority Data
Sep. 12, 2008 (FR) ...................................... 08 56164

(51) Int. Cl.
*A61F 2/00* (2006.01)
(52) U.S. Cl.
USPC .......................................... 523/115; 523/113
(58) Field of Classification Search
USPC .................................................. 523/113, 115
See application file for complete search history.

(56) References Cited

U.S. PATENT DOCUMENTS

| | | | | |
|---|---|---|---|---|
| 2,463,549 A * | 3/1949 | Myerson | ...................... | 433/191 |
| 3,423,828 A * | 1/1969 | Halpern et al. | ................ | 523/115 |
| 3,672,942 A * | 6/1972 | Neumann et al. | ............. | 427/295 |
| 4,479,986 A * | 10/1984 | Juday | ............................. | 427/295 |
| 5,250,352 A | 10/1993 | Tyszblat | | |
| 5,656,710 A * | 8/1997 | Newberth et al. | ................ | 528/14 |
| 5,843,348 A | 12/1998 | Giordano | | |
| 5,869,548 A | 2/1999 | Ikushima et al. | | |
| 6,203,911 B1 | 3/2001 | Weberg et al. | | |
| 6,652,270 B1 * | 11/2003 | Hogan | ............................. | 432/12 |
| 6,913,650 B2 * | 7/2005 | Gilmore et al. | ................. | 118/66 |
| 7,294,392 B2 | 11/2007 | Aechtner et al. | | |
| 7,323,222 B2 * | 1/2008 | Luong et al. | ............... | 427/385.5 |
| 7,503,976 B2 * | 3/2009 | Gilmore et al. | ................. | 118/66 |
| 2004/0112507 A1 * | 6/2004 | Luong et al. | ................... | 156/145 |
| 2006/0199876 A1 * | 9/2006 | Troczynski et al. | .......... | 523/115 |

FOREIGN PATENT DOCUMENTS

| | | |
|---|---|---|
| CH | 511 599 | 8/1971 |
| EP | 0 240 643 A1 | 10/1987 |
| EP | 0 241 384 A2 | 10/1987 |
| EP | 0 701 808 A2 | 3/1996 |
| FR | 2 725 358 | 4/1996 |
| FR | 2 904 306 A1 | 2/2008 |
| GB | 911 549 | 11/1962 |
| JP | A-63-252981 | 10/1988 |
| JP | A-05-319959 | 12/1993 |
| JP | A-09-098990 | 4/1997 |
| JP | A-10-043209 | 2/1998 |
| JP | A-2001-279106 | 10/2001 |
| WO | WO 93/07846 | 4/1993 |
| WO | WO 94/12448 | 6/1994 |
| WO | WO 00/40206 | 7/2000 |
| WO | WO 2005/042623 A1 | 5/2005 |

OTHER PUBLICATIONS

NPL article titled Table of Hardness Values, Appendix 1, The Open University, 2012. Author Unknown.*
French Search Report dated Jun. 16, 2009 issued in French Patent Application No. 0856164 (with translation).
French Written Opinion dated Sep. 12, 2008 issued in French Patent Application No. 0856164 (with translation).
Translation of the Examiner's Comments from the Japanese Office Action issued Dec. 24, 2012 Including Current Pending Claims (English Translation Only).

* cited by examiner

*Primary Examiner* — James J Seidleck
*Assistant Examiner* — Peter A Salamon
(74) *Attorney, Agent, or Firm* — Oliff & Berridge, PLC

(57) ABSTRACT

Methods of producing a composite block intended for the production of a dental prosthesis including the following steps: a) impregnating a porous support with a liquid resin and b) curing the liquid resin impregnating the support are provided. In such methods of producing a composite block intended for the production of a dental prosthesis, a volume of liquid resin that is greater than the volume of the open pores of the support by at least 2% is caused to penetrate into the support and to cure therein, said volumes being measured at a temperature of 20° C. and at a pressure of 1 bar.

15 Claims, No Drawings

COMPOSITE CERAMIC BLOCK

FIELD OF THE INVENTION

The invention relates to a method of producing a composite block intended for the production of a dental prosthesis and to a method of producing a dental prosthesis. The invention also relates to a composite block and to a dental prosthesis obtained or that is capable of being obtained by such methods.

PRIOR ART

Composite blocks are known that comprise a porous support, generally formed from a sintered ceramic material, and a resin that at least partially fills the interstices of the support.

In order to produce such a composite block, liquid resin is infiltrated into the accessible or "open" pores of a support, generally by capillary action. After curing the resin, the composite block obtained is machined to the desired definitive form, conventionally by CAD-CAM (computer-aided design-computer aided machining).

Methods of producing composite blocks are described in particular in the following documents: U.S. Pat. No. 5,869,548, U.S. Pat. No. 5,843,348, U.S. Pat. No. 5,250,352, European patent EP-A-0 241 384, International patent WO-A-93/07846, FR 2 725 358, EP-A-0 240 643, French patent FR-A-2 904 306, EP-A-0 701 808, and U.S. Pat. No. 7,294,392.

Composite blocks produced using current methods, however, have insufficient strength. In particular, the resin tends to become detached from the support. Until now, said low strength has prevented commercial exploitation of such composite blocks in the production of dental prostheses.

An object of the invention is to provide a novel method that can improve the properties of composite blocks, in particular by increasing their strength.

SUMMARY OF THE INVENTION

In accordance with the invention, this object is achieved by a method of producing a composite block intended for the production of a dental prosthesis, said method comprising the following steps:
  a) infiltrating a porous support with a liquid resin;
  b) curing the liquid resin impregnating the support.

This method is remarkable in that in step b), the resin is subjected to a pressure of more than 300 bar. As can be seen from the description below, a method of the invention can produce composite blocks having enhanced strength.

Without wishing to be bound by this theory, the inventor explains the performances obtained by the fact that exerting the pressure would allow, beyond the sole compensation of the potential shrinkage of the resin during its curing, placing of the solid resin under compression, i.e. the creation of a pre-stress that increases its strength.

Preferably, a volume of liquid resin $V_L$ that is at least 2%, preferably at least 5%, more preferably at least 10% or even at least 15% greater than the volume $V_P$ of the open pores of the support is caused to penetrate into the support and to cure therein, said volumes $V_L$ and $V_P$ being measured at a temperature of 20° C. and at a pressure of 1 bar.

The infiltrated liquid resin may in particular be subjected to a pressure of more than 400 bar, preferably more than 500 bar, more than 1000 bar, more than 2000 bar, more than 3000 bar more than 4 000 bar, or even more than 5000 bar. These high pressures increase the density of the liquid resin and the material constituting the support. However, the compressibility of the liquid resin is greater than that of the material constituting the support. The quantity of liquid resin that can be infiltrated per unit volume of open pores is thus greater than that which could be infiltrated by only applying lower pressures, in particular atmospheric pressure. In the remainder of the description, unless indicated otherwise, the term "pressure" indicates the high pressure mentioned above. By default, the word "pressure" thus does not designate "atmospheric pressure".

The pressure must be exerted on the resin infiltrated into the support while it is still liquid and until it is at least partially cured. Preferably, all of the liquid resin impregnating the support is cured before returning to atmospheric pressure. Preferably, the pressure is kept substantially constant until all of the infiltrated resin has been cured.

The pressure may also be exerted during all or part of the infiltration phase that advantageously facilitates penetration of the liquid resin, and thus allows more-viscous resins to be used.

Preferably, the pressure is exerted isostatically or "uniaxially". Any known method of placing under pressure may be used.

Alternatively to the pressurization described above or preferably as a complement to this pressurization, infiltration of the liquid resin, if appropriate under pressure, is continued while curing the resin that has already infiltrated; preferably again, curing is controlled such that it is carried out from the interior of the support towards its periphery. Thus, advantageously, the cured resin does not resist penetration of the additional liquid resin within the support. Thus, it is possible to compensate for shrinkage of the resin during its curing, and, beyond, to place the solid resin under compression.

To control curing, it is possible in particular to operate on one or more of the following parameters:
  the concentration of accelerator and/or catalyst in the liquid resin;
  the temperature and duration over which this temperature is held;
  the chemical nature of the resin.

Preferably, the optimum conditions, in particular the pressure that may be employed in step b) and possibly in step a), are determined as a function of the resin and the support by measuring the homogeneity of its micro-harness, its strength and its optical properties.

Preferably, the support is shaped such that the composite block may be machined using a CAD-CAM device, in particular using a machining device such as the CELAY® system from Mikrona or CEREC 3 from SIRONA. If appropriate, the support may integrate one or more means allowing it to be held by such devices.

The support may present the general shape of a dental prosthesis.

The invention is not limited by its chemical nature or the general shape of the support as long as it is porous and comprises interconnected open pores, which also extend through its mass.

Preferably, before infiltration, the support has an apparent porosity of more than 15%, measured using International standard ISO 5017. Preferably again, the support has an apparent porosity in the range 25% to 50%. The largest pore diameter is preferably in the range 0.2 micrometers (μm) to 2 μm. Examples of suitable supports are those sold by VITA ZAHNFABRIK.

The support may present the shape of a tooth.
The support may be in a porous ceramic material.

The support is preferably formed from a sintered material, preferably selected from a metal oxide in the form of a glass-ceramic, a glass, or a crystalline ceramic such as quartz, alumina, or mullite.

Preferably again, before impregnation, the compactness of the support is more than 60% and/or less than 90%.

In a particular implementation, the support results from sintering at a temperature in the range 1100° C. to 1400° C., for a period in the range 2 hours (h) to 10 h, of a preform based on alumina. The temperature ramp-up may, for example, be in the range 60° C./h to 300° C./h.

The resin may be a monomer or a mixture of monomers.

Preferably, the liquid resin only comprises a mixture of monomer and catalyst.

Preferably, the resin is chemopolymerizable, thermopolymerizable, or thermoplastic.

In particular, the resin may be selected from the polymerizable resins described in U.S. Pat. No. 5,869,548, U.S. Pat. No. 5,843,348, and EP-A-0 0 701 808.

Preferably, the resin is selected from the following list:
 a chemopolymerizable or thermopolymerizable resin monomer, preferably a vinyl ester or acrylic resin. In particular, the resin may be selected from the group formed by 2-Hydroxyethyl methacrylate, CAS 868-77-9 (HEMA), Tetraethylene glycol dimethacrylate CAS 109-17-1, (TEGDMA), 2,2-bis-(4-(2-hydroxy-3-methacryloyloxy-propoxy)phenyl)propane, CAS 1565-94-2 (BIS-GMA), urethane dimethacrylate 1,6-bis (methacryloxy-2-ethoxycarbonylamino)-2,4,4-trimethylhexane (UDMA), CAS 72869-86-4, ethylene glycol dimethacrylate (EGDMA), diethylene glycol dimethacrylate (DEGDMA), and Bisphenol A-dimethacrylate, CAS 109-17-1 (BADMA);
 a thermoplastic resin, in particular selected from saturated polyesters, especially polyethylene terephtalate (PET) and Poly(1,4-butylene terephtalate), CAS 24968-12-5 (PBT), Poly(bisphenol A carbonate) polycarbonates, CAS 25037-45-0 (PC), bisphenol A carbonate, and polyamides.

The nature of the resin is not limiting.

In a preferred embodiment, the liquid resin does not comprise particles having a size greater than 0.1 mm, greater than 0.5 mm, or greater than 1 mm.

In an embodiment, the liquid resin does not comprise pigment (particle having a nanometric size), even does not comprise solid particles.

To facilitate the penetration of the liquid resin, it is in fact preferable that it presents a low viscosity. In particular, it should not present a pasty nature.

In order to catalyze the chemopolymerizable impregnation materials it is possible to use peroxides, in particular Dibenzoylperoxide, CAS 94-36-0, Methyl Ethyl Ketone Peroxides, CAS 1338-23-4, Di-tert-amyl peroxide, CAS 10508-09-5, Di-tert-butylperoxide, CAS 110-05-4, or Cumene Hydroperoxide, CAS 80-15-9.

In order to accelerate curing with dibenzoyl peroxide, CAS 94-36-0, dimethylaniline (DMA), diethylaniline (DEA) or dimethyl para-toluidine (DMPT) may be used. In order to accelerate curing with Methyl Ethyl Ketone Peroxides, CAS 1338-23-4, it is possible in particular to use Cobalt (II) 2-ethylhexanoate.

If appropriate, the composite block undergoes a suitable heat treatment to bring about polymerization, for example at 100° C. for one hour.

After curing the resin, a composite block is obtained that has hardness that may exceed 140 Vickers, which is greatly superior to the hardness of current composite blocks, at about 60 Vickers.

The invention also provides a method of producing a dental prosthesis, comprising an operation for machining a composite block produced using a method in accordance with the invention. The support is thus machined to its definitive shape after incorporating the resin.

The invention also provides a composite block and a dental prosthesis that is produced or that may be produced using a method in accordance with the invention.

Preferably, a composite block of the invention has hardness of more than 100 Vickers, preferably more than 120 Vickers, or even more than 140 Vickers.

Preferably, a composite block of the invention has a Young's modulus of more than 25 gigapascals (GPa), measured using the International standard ISO 10 477, and/or a three-point bending modulus of more than 120 megapascals (MPa) measured using the standard ISO 6 872.

DEFINITIONS

The term "dental prosthesis" in general means any part intended to be placed in the set of teeth of a patient with the aim of restoring it in its entirety or partially to its natural form.

For this reason, the dental prostheses produced in accordance with the invention may, for example, be caps or crowns that are placed on the stump of a natural tooth, or prostheses generally designated as inlays or onlays that are intended to reconstitute partial damage to a tooth by filling the cavity resulting from a loss of tooth substance by means of a part having the same shape and produced by the prosthetist, or bridges that are prostheses which bear simultaneously on the subsisting portions of at least two teeth, possibly thereby compensating for one or more missing teeth.

Depending on the nature of the dental prosthesis produced, a composite block in accordance with the invention may be rendered integral with other parts, for example with a metal base.

DETAILED DESCRIPTION

In the prior art, a liquid resin will fill the open pore volume, $V_P$ (L), by capillary action, conventionally at ambient pressure. The volume of liquid resin infiltrated into the support, $V_L$ (L), is thus substantially equal to the open pore volume, $V_P$ (L), at ambient pressure.

On curing, the resin shrinks such that the volume occupied by the solid resin, $V_M$ (L), is smaller than the open pore volume, $V_P$ (L). As an example, the shrinkage resulting from polymerization at ambient temperature may conventionally result in a reduction in the volume occupied by the resin that is in the range 6% to 15% of its initial volume.

This results in high tensile stresses at the interface between the resin and the surface of the support defining the pores, which results in detachment of the resin and thus in a reduction in the service life of the dental prosthesis, rendering it unsuitable for commercial use.

According to the invention, a vacuum is preferably created in the support before commencing infiltration of the liquid resin. This vacuum preferably corresponds to a pressure of less than 200 millibars (mbar), preferably less than 100 mbar. Advantageously, the vacuum encourages penetration of the liquid resin.

The liquid resin may be infiltrated at atmospheric pressure or at a pressure that is higher than atmospheric pressure.

Infiltration at atmospheric pressure is advantageously simple to carry out, but requires the use of a liquid resin of low viscosity. High pressure infiltration is also possible and may even be necessary if the viscosity of the liquid resin is too high. Regardless of the pressure at which infiltration is carried out, in a particularly preferred implementation of the invention, it is possible to subject the liquid resin that has penetrated into the support to a high pressure of more than 300 bar until at least a portion, and preferably all, of said resin has been cured.

The difference in compressibility between the materials used for the support and for the liquid resin advantageously allows an additional volume of liquid resin to be infiltrated that is higher than that which can be infiltrated at atmospheric pressure. By curing the liquid resin under pressure, it then becomes possible, after returning to atmospheric pressure, to create pre-stresses tending to compress the resin. This results in considerably improved strength.

Further, and still in a preferred implementation of the invention, particularly when curing is relatively slow, curing of the resin is controlled in a manner such that it is carried out from the interior towards the exterior of the support. In other words, resin that has already hardened does not oppose the infiltration of additional resin, which compensates for the reduction in volume occupied by the infiltrated resin due to curing thereof.

In particular, the resin may be a chemopolymerizable resin, conventionally mixed with a catalyst and an accelerator, infiltrated, for example, at a pressure of 500 bar and at a temperature in the range 80° C. to 100° C.

The resin may also be a thermoplastic resin that, for example, is infiltrated at an isostatic pressure of 2500 bar, at 250° C., into a support that has been placed under vacuum and heated to 250° C. The thermoplastic resin may also be infiltrated, for example, at a pressure of 3500 bar, at a temperature of 300° C., into a support that has been placed under vacuum and heated to a temperature of 300° C.

Various methods can be used to control the curing as a function of the resin used.

As an example, when the resin is chemopolymerizable, it is possible to add thereto a varying quantity of accelerator. At the start of infiltration, for example, it is possible to infiltrate a resin comprising a high quantity of accelerator then, as infiltration progresses, to reduce the concentration of accelerator in the infiltrated resin.

The nature of the resin may also be varied. As an example, when commencing infiltration, it is possible to infiltrate a first thermopolymerizable resin at a first temperature then to infiltrate a second thermopolymerizable resin at a second temperature that is higher than the first temperature. As an example, infiltration may commence with benzoyl peroxide, which is polymerizable at 80° C., then continued with di-t-butyl-1,2,1-peroxide or di-t-amyl-1,4,2-peroxide or comyl-1,8,8-peroxide, which are polymerizable at 120° C. In order to control curing, it is then sufficient to heat the support to a temperature in the range 80° C. to 120° C., for example to 90° C., to cure only the first resin in the core of the support, then to heat the support to more than 120° C. to cure the second resin at the periphery. Infiltration at a pressure of approximately 2000 bar is advantageous.

In a variation, it is possible to initially infiltrate the core of the support with a chemopolymerizable resin, for example a first resin mixed with a catalyst and an accelerator then, at its periphery, with a thermopolymerizable resin, for example a second resin mixed with a catalyst. Curing the peripheral resin may then be carried out by heating, for example, between 80° C. and 100° C. after curing the resin disposed in the core of the support. Infiltration at a pressure of approximately 1500 bar is advantageous.

All of the infiltrated resin is preferably cured before returning to ambient pressure. This return to ambient pressure is accompanied by expansion of the volumes of the support and the solid resin.

Unlike blocks produced using prior art techniques, the composite block obtained does not contain mechanical stresses that have a tendency to detach the resin from the support (tensile stresses on the resin). In contrast, the "excess volume" of infiltrated and cured resin is preferably determined as a function of the resin and the support in order to create a pre-stress, i.e. a permanent pressure between the solid resin and the support. In other words, the solid resin is preferably compressed by the sintered support. The strength of the composite block is considerably augmented thereby.

Further, the optical properties of the composite block render it entirely suitable for use as a dental prosthesis after optional final machining.

A method of producing a composite dental prosthesis in accordance with the invention may comprise the following steps:
1) preparing a porous support;
2) optionally, rectifying the shape of the porous support;
3) optionally, a silanation treatment at the surface of the open pores of the porous support;
4) impregnating the porous support with a liquid resin;
5) curing the liquid resin that has been infiltrated into the porous support, optionally followed by a consolidating heat treatment;
6) final shaping.

In step 1), current porous support production methods, in particular those described in the above-mentioned documents, may be used. Preferably, the porous support is as described above.

The silanation treatment in step 3) is intended to increase the wettability of the pore surface by the liquid resin, and in particular is intended to render said surface more hydrophobic. Preferably, this silanation treatment comprises silanation using an alkoxysilane or a halosilane, preferably 3-methacryloxy-propyltrimethoxysilane. After application of the silanation agent, the support is dried, preferably at a temperature in the range 100° C. to 200° C., conventionally for several hours.

The silanation treatment may, for example, be carried out in accordance with the method described in U.S. Pat. No. 5,869,548.

Steps 4) and 5) correspond to steps a) and b) of a method of producing a composite block of the invention, as described above.

EXAMPLES

The following examples are provided for illustrative and non-limiting purposes.

Example 1

The porous support resulted from sintering, at 1050° C. for 2 h, a preform formed from an alkali aluminosilicate glass powder with a particle size in the range 5 μm to 20 μm. After sintering, the compactness of the support was 60%.

The porous support underwent, in succession:
a silanation treatment using a solution with the following composition, given as percentages by weight:
methoxypropanol: 93.8%
water: 5%
acetic acid: 0.2% silane: 1%
drying at 150° C. for 4 h;
placing under vacuum;
infiltrating with a resin at a temperature of 20° C. at a pressure of 500 bar, for 15 minutes, the composition by weight of said resin being as follows:
BIS-GMA: 60%
TEGDMA: 39.36%
Methylethylketone peroxide: 0.6%
Cobalt octoate: 0.04%
heating, still at a pressure of 500 bar, for 2 h at 60° C.

In practice it is possible, after the silanation operation, to place the porous structure in a latex mold, apply a vacuum, for example to a pressure of approximately 100 mbar, then to introduce the liquid resin under vacuum and to close the mold. The closed mold may then be introduced into a crucible or an autoclave where it is progressively subjected to a pressure of 500 bar. The pressure is then maintained to equilibrium. The mold may then undergo consolidation heating before cooling and returning it to atmospheric pressure.

Example 2

The porous support resulted from sintering, at 1150° C. for 2 h, a preform formed from a lithium disilicate glass-ceramic powder with a particle size in the range 1 μm to 20 μm. After sintering, the compactness of the support was 65%.

The porous support underwent, in succession:
a silanation treatment and drying treatment identical to those of Example 1;
placing under vacuum;
infiltrating by capillary action with a first resin at a temperature of 20° C. at a pressure of 1 bar (ambient air) for 10 minutes, the composition by weight of said first resin being as follows:
EBADMA: 99.12%
Ethoxylated bisphenol-A dimethacrylate CAS 41637-38-1:
Benzoyl peroxide: 0.8%
DMPT: 0.08%
immersion in a second resin with application of a pressure of 1000 bar to the surface of said resin for 20 minutes at a temperature of 20° C., the composition by weight of said second resin being as follows:
UDMA: 80%
TEGDMA: 19.192%
Benzoyl peroxide: 0.8%
DMPT: 0.04%
placing under pressure of 1000 bar for 1 h; then
heating, for 1 h at 80° C.;
cooling to ambient temperature;
reducing the pressure to ambient pressure.

Example 3

The porous support resulted from sintering, at 1100° C. for 2 h, a preform formed from an alkali aluminosilicate glass powder charged with crystals of albite $NaAlSi_3O_8$ with a particle size of approximately 10 μm. After sintering, the compactness of the support was 72%.

The porous support underwent, in succession:
a silanation treatment and drying treatment identical to those of Example 1;
placing under vacuum;
infiltrating by capillary action with a first chemopolymerizable resin at a temperature of 20° C., a pressure of 500 bar for 15 minutes, the composition by weight of said first resin being as follows:

UDMA: 98.95%
MEKP: 1%
Cobalt octoate: 0.05%
immersing in a second, thermopolymerizable, resin with application of a pressure of 2000 bar, using water, to the surface of said resin for 30 minutes at a temperature of 40° C., the composition by weight of said second resin being as follows:
UDMA: 98%
MEKP: 2%
heating, still at a pressure of 2000 bar, for 2 h at 100° C.;
cooling to ambient temperature;
reducing the pressure to ambient pressure.

Example 4

The porous support resulted from sintering, at 1200° C. for 2 h, a preform formed from a ceramic and quartz, $SiO_2$, powder with a particle size in the range 0.1 μm to 10 μm. After sintering, the compactness of the support was 78%.

The porous support underwent, in succession:
a silanation treatment and drying treatment identical to those of Example 1;
placing under vacuum;
infiltrating by capillary action, at a pressure of 1 bar, with a first thermopolymerizable resin (monomer mixture) at a temperature of 40° C., the composition by weight of said first resin being as follows:
EBADMA: 99%
Ethoxylated bisphenol-A dimethacrylate CAS 41637-38-1:
Benzoyl peroxide: 1%
leaving, in ambient air, for 20 minutes;
immersing in a second thermopolymerizable resin, applying a pressure of 3000 bar to the surface of said resin for 15 minutes, the composition by weight of said second resin being as follows:
BIS-GMA: 80%
TREGDMA: 18%
Di-t-butyl peroxide: 2%
heating, still at a pressure of 5000 bar, for 1 h at 90° C.;
heating, still at a pressure of 5000 bar, for 1 h at 130° C.;
cooling to ambient temperature;
reducing the pressure to ambient pressure.

Example 5

The porous support resulted from sintering, at 1500° C. for 2 h, a preform formed from a powder of mullite, $(Al_2O_3).2(SiO_2)$) with a particle size in the range 0.1 μm to 10 μm. After sintering, the compactness of the support was 76%.

The support underwent, in succession:
placing under vacuum;
bringing into contact with granules of amorphous polyethylene terephthalate polymer;
heating to 250° C. until the whole surface of the preform was wetted with the liquid polymer;
applying a pressure of 3000 bar using a gas (air or air-argon), for 60 minutes at a temperature of 250° C.;
cooling to ambient temperature;
reducing the pressure to ambient pressure.

Example 6

The porous support resulted from sintering, at 1300° C. for 2 h, a preform formed from alumina ($Al_2O_3$) powder with a particle size in the range 0.1 µm to 30 µm. After sintering, the density of the support was 84%.

The support underwent, in succession:
placing under vacuum;
bringing into contact with granules of polycarbonate (bisphenol A carbonate);
heating to 300° C. under vacuum for 30 minutes to wet and coat the whole surface of the preform with liquid polycarbonate;
applying a pressure of 2000 bar using a gas (air or air-argon) for 30 minutes, keeping the temperature at 300° C.;
cooling to ambient temperature;
reducing the pressure to ambient pressure. Clearly, the invention is not limited to the implementations described and shown. In particular, infiltration of the liquid resin may be limited to a limited region of the support, and in particular may be limited to its peripheral region.

The term "comprising a" should be construed as meaning "comprising at least one".

The invention claimed is:

1. A method of producing a composite block intended for the production of a dental prosthesis, said method comprising the following steps:
   a) infiltrating a porous support made in a material with a quantity of a liquid resin; and
   b) curing the liquid resin impregnating the support, wherein, in step b), the liquid resin is subjected to a pressure of more than 300 bar,
   wherein the pressure and a difference in compressibility between the material of the porous support and the liquid resin makes a volume quantity of the liquid resin infiltrated into the porous support exceed the volume of open pores of the porous support by greater than or equal to 2%, the volumes of the liquid resin and of the open pores being measured at a temperature of 20° C. and a pressure of 1 bar.

2. A method according to claim 1, wherein said volume of liquid resin is greater than said volume of open pores by at least 10%.

3. A method according to claim 2, wherein said volume of liquid resin is greater than said volume of open pores by at least 15%.

4. A method according to claim 1, wherein said pressure is greater than 2000 bar.

5. A method according to claim 4, wherein said pressure is greater than 4000 bar.

6. A method according to claim 1, wherein the porous support is a sintered material, presents an open porosity higher than 15% and less than 50%, and has the shape of a tooth.

7. A method according to claim 1, wherein, prior to infiltration, a vacuum is created in the support.

8. A method according to claim 1, wherein infiltration of liquid resin, if necessary under pressure, is continued during curing of the liquid resin that has already been infiltrated, and curing of said liquid resin that has already been infiltrated is controlled such that it is carried out from the interior of the support towards its periphery.

9. A method according to claim 8, wherein, in order to control said curing, one or more of the following parameters is operated upon:
   the concentration of accelerator or catalyst in the liquid resin;
   the temperature and/or duration over which the temperature is maintained;
   the chemical nature of the resin.

10. A method according to claim 1, wherein all of the liquid resin impregnating the support is cured before returning to atmospheric pressure.

11. A method according to claim 1, wherein the liquid resin is chemopolymerizable, thermopolymerizable or thermoplastic.

12. A method of producing a dental prosthesis, comprising an operation for machining a composite block produced using a method in accordance with claim 1.

13. The method according to claim 1 wherein the composite block has a Vickers hardness of more than 100.

14. The method according to claim 13 wherein the composite block has a Vickers hardness of more than 140.

15. The method according to claim 13 wherein the composite block has a Young's modulus of more than 25 GPa, measured in accordance with International standard ISO 10 477, and/or a three-point bending modulus of more than 120 MPa, measured in accordance with ISO 6 872.

* * * * *